United States Patent
Mullaly et al.

(10) Patent No.: US 6,981,871 B2
(45) Date of Patent: Jan. 3, 2006

(54) DENTAL ATTACHMENT ASSEMBLY AND METHOD

(75) Inventors: Scott Mullaly, San Marcos, CA (US); Paul T. Zuest, Escondido, CA (US)

(73) Assignee: Zest Anchors, Inc., Escondido, CA (US)

( * ) Notice: Subject to any disclaimer, the term of this patent is extended or adjusted under 35 U.S.C. 154(b) by 202 days.

(21) Appl. No.: 10/190,921

(22) Filed: Jul. 5, 2002

(65) Prior Publication Data

US 2004/0005530 A1 Jan. 8, 2004

(51) Int. Cl.
*A61C 13/225* (2006.01)

(52) U.S. Cl. ........................... 433/172; 433/181
(58) Field of Classification Search ............... 433/172, 433/181, 177, 182, 178, 191, 173
See application file for complete search history.

(56) References Cited

U.S. PATENT DOCUMENTS

| | | | |
|---|---|---|---|
| 3,514,858 A | 6/1970 | Silverman | |
| 3,787,975 A | 1/1974 | Zuest | |
| 3,991,472 A | 11/1976 | Lukesch | |
| 4,290,755 A | 9/1981 | Scott | |
| 4,362,509 A * | 12/1982 | Sulc | 433/181 |
| 4,475,891 A * | 10/1984 | Hader | 433/181 |
| 4,488,874 A | 12/1984 | Soifer | |
| 4,540,367 A | 9/1985 | Sulc | |
| 4,547,156 A | 10/1985 | Hader | |
| 4,626,213 A | 12/1986 | Shiner et al. | |
| 4,793,808 A | 12/1988 | Kirsch | |
| 4,854,872 A | 8/1989 | Detsch | |
| 4,957,438 A * | 9/1990 | Bax | 433/180 |
| 4,988,297 A | 1/1991 | Lazzara et al. | |
| 5,030,095 A | 7/1991 | Niznick | |
| 5,049,072 A | 9/1991 | Lueschen | |
| 5,120,222 A | 6/1992 | Sulc | |
| 5,194,000 A | 3/1993 | Dury | |
| 5,195,891 A | 3/1993 | Sulc | |
| 5,211,561 A | 5/1993 | Graub | |
| 5,413,480 A | 5/1995 | Musikant et al. | |
| 5,417,570 A | 5/1995 | Zuest | |
| 5,520,540 A | 5/1996 | Nardi | |

(Continued)

FOREIGN PATENT DOCUMENTS

EP 0037864 A1 10/1981

(Continued)

OTHER PUBLICATIONS

Lindberg Homburger Modent Dental Preci-Clix Attachment, p. 80, Canadian Journal of Dential Technology, Fall 2000.

*Primary Examiner*—Melba N. Bumgarner
(74) *Attorney, Agent, or Firm*—Gordon & Rees LLP

(57) ABSTRACT

A dental attachment assembly has an abutment member for attachment to a tooth root, implant, adjacent tooth, or bar, and a retention member for hinged engagement in a cap secured in a dental appliance. A skirt projects from one end of the cap for releasable snap engagement over an outer locating surface on the abutment member. The outer locating surface has at least two axially spaced retention surfaces for mating, snap engagement with corresponding spaced snap engagement formations on the inner surface of the cap, to provide a stacked, external retention between the abutment and retention members.

16 Claims, 3 Drawing Sheets

U.S. PATENT DOCUMENTS

| | | | |
|---|---|---|---|
| 5,527,182 A * | 6/1996 | Willoughby | 433/172 |
| 5,556,280 A | 9/1996 | Pelak | |
| 6,030,219 A | 2/2000 | Zuest | |
| 6,299,447 B1 | 10/2001 | Zuest | |
| 6,332,777 B1 | 12/2001 | Sutter | |

FOREIGN PATENT DOCUMENTS

| | | |
|---|---|---|
| EP | 0 501 940 A1 | 2/1992 |
| WO | WO 92/10145 | 6/1992 |
| WO | 03/19190 | 6/2003 |

* cited by examiner

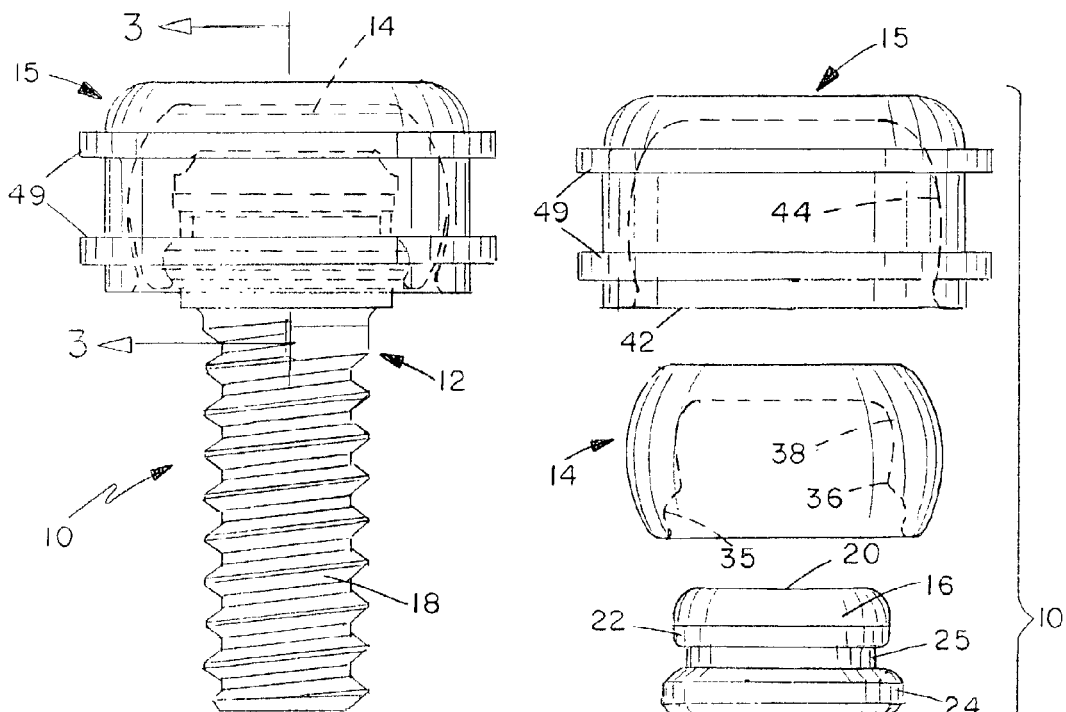

DENTAL ATTACHMENT ASSEMBLY AND METHOD

BACKGROUND OF THE INVENTION

The present invention relates to a dental attachment or anchoring structure for attaching a dental appliance such as a full denture, overdenture, partial denture, or the like to a remaining non-vital root, an adjacent tooth, or to an endosseus implant.

Dental anchoring assemblies are known in which a female part is provided for attachment to a root, implant, or adjacent tooth, and a male part is engaged in a recess in a dental appliance, the male and female parts having mating, snap engageable formations for releasably securing the male part to the female part. For example, in U.S. Pat. No. 5,417,570 of Zuest, the female part has a socket and the male part has a head for snap engagement in the socket. However, users may find it difficult to properly locate the male head in the female socket, such that the head may hit the periphery of the socket in some cases. Repeated impacts of this nature may damage the retentive head of the male, causing it to lose some of its retention ability.

U.S. Pat. Nos. 6,030,219 and 6,299,447 of Zuest et al. describe dental attachment assemblies in which the male part has a skirt for snap engagement over an outer locating surface of the female or abutment member. The male part may also have a central stem for snap engagement in a socket in the female part, providing both inner and outer retention surfaces, and therefore increased retention force. It is also easier to locate the male part properly over the female part. However, these parts are of a relatively large diameter which is not suitable for anterior teeth or for locations in a denture corresponding to the smallest teeth.

SUMMARY OF THE INVENTION

It is an object of the present invention to provide a new and improved dental attachment assembly and method.

According to one aspect of the present invention, a dental attachment assembly is provided, which comprises an abutment member for attachment to a tooth root, implant, or adjacent tooth, the abutment member having a central axis, a first end, and an outer locating surface projecting away from the first end, the outer locating surface having at least two axially spaced retention portions, and a retention member having a first end and a skirt extending from the first end having an inner surface for engagement over the outer locating surface of the abutment member, the inner surface of the skirt having at least two axially spaced, snap engaging formations for releasable snap engagement with the respective retention portions of the abutment member.

The abutment member may have a head on which the spaced retention portions are located, with a stem extending axially away from the head for engagement in a socket in a tooth root or implant, or may be designed for anchoring to an adjacent tooth, in which case it has a radial extension for securing to an adjacent tooth. Two or more spaced retention portions may be provided. In one embodiment, the spaced retention portions on the outer locating surface or head of the abutment member comprise generally rounded, annular projections, while the inner surface of the skirt of the retention member comprise correspondingly spaced, annular indents or grooves for snap engagement over the projections. Alternatively, the head of the abutment member may have spaced grooves while the inner surface of the skirt has spaced, annular inwardly directed projections or ribs for snap engagement in the grooves.

The provision of multiple stacked retention surfaces between the abutment or "male" member and the retention or "female" member allows a greater retention wear surface area with a smaller overall diameter than is necessary with previous attachments which had both inner and outer retention. Thus, the need to provide a socket in the member attached to the tooth or implant, and a corresponding stem on the member attached to the denture for snap engagement in the socket can be avoided, while still providing a similar retention force by the provision of stacked, external retention surfaces. This permits the attachment assembly to be of a smaller overall diameter than was necessary in previous designs where the denture part of the attachment had both a skirt and internal stem. Thus, the assembly can be used for portions of a denture corresponding to smaller, anterior teeth.

The retention or female member is of generally inverted cup-like shape in an exemplary embodiment, and the skirt has a rounded lower rim which assists in proper alignment as the female part is pushed down onto the abutment member. This is an improvement over prior art arrangements where the retention member had a flat or square lower edge or rim, which would catch on the abutment member and tend to curl inwards, sometimes preventing the retention member from seating properly.

The retention portions may be of the same diameter. However, in an exemplary embodiment of the invention, the uppermost retention portion closest to the first end of the male member has a diameter which is slightly less than that of the lower retention portion or portions. This will allow the female member to snap over the first rib with less force required, allowing for easier seating of the attachment by the patient. The lowest rib or retention portion is of slightly greater diameter to have more retentive hold than the or each rib above it, thus holding the denture more securely in place against accidental dislodgement. This arrangement will make the denture easier to insert or place than to remove.

In an exemplary embodiment of the invention, a cap or housing secured in the dental appliance pivots over the female or retention member. The cap has an inner curved surface for snap engagement over the outer surface of the female or retention member, retaining the female member and preventing it from accidentally coming out as the denture is removed. The curvature is such that the female member can be relatively easily inserted into the cap, but, once inserted, the female member is held tight against accidental removal.

In one embodiment of the invention, the male or abutment member is designed for distal attachment to an adjacent tooth, rather than co-axial attachment to an underlying tooth root or implant. In this assembly, the male or abutment member has a radial or distal extension from one side of its outer locating surface, and a plate at the outer end of the extension for securing in the adjacent tooth surface. The female or retention member and cap both have slots for engaging over the distal extension to allow the retention member skirt to engage over the outer locating surface. The female or retention member has an upper flat, generally horizontal surface portion above the slot, while the cap has a downwardly facing, generally horizontal surface portion at the upper end of its slot. These surface portions together form a horizontal stop to prevent uplift of the partial denture. The opposing surface portions are designed so that the pivoting cap housing will contact and stop on the opposing surface of the female member, thus preventing any further pivoting and potential uplift of the denture. This stop arrangement also prevents the pivoting cap from contacting the abutment tooth.

The dental attachment assembly of this invention uses stacked retention surface between the male or abutment part attached to the tooth, tooth root or implant and the female or retention part attached to the dental appliance. This provides a greater retention wear surface area with a smaller diameter, allowing use with smaller, anterior teeth and also increasing the effective lifetime of the assembly, reducing loss of retention force.

BRIEF DESCRIPTION OF THE DRAWINGS

The present invention will be better understood from the following detailed description of some exemplary embodiments of the invention, taken in conjunction with the accompanying drawings in which like reference numerals refer to like parts and in which:

FIG. 1 is a side view of the assembled dental attachment according to a first embodiment of the invention;

FIG. 2 is a side view of the separated components of the attachment;

FIG. 3 is an enlarged sectional view taken on line 3—3 of FIG. 1;

FIG. 4 is a side view of an implant abutment screw configuration;

DETAILED DESCRIPTION OF THE DRAWINGS

Figure 5:
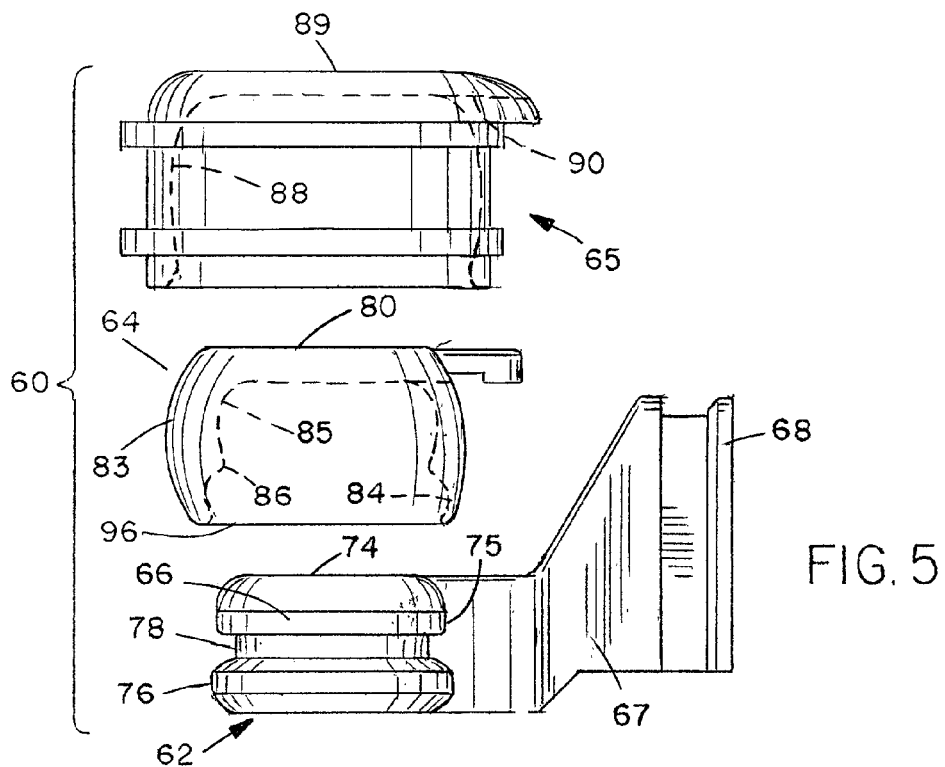
FIG. 5 is a side view of the separated components of a dental attachment assembly according to another embodiment of the invention.

FIGS. 1 to 3 illustrate a dental attachment or anchor assembly 10 securing a dental appliance such as a partial denture to a remaining non-vital root. The assembly 10 basically comprises a male or abutment member 12, a female or retention member 14, and a cap 15 for securing in a suitable indent in the denture. The male member 12 will be of a suitable strong metal material such as stainless steel with titanium nitride coating, while the female member is of a material having some resilience, such as nylon, and the cap is of metal such as stainless steel.

The male or abutment member 12 has an enlarged head 16 and a threaded shaft or stem 18 extending from the head for attachment in a prepared bore in a tooth root in a conventional manner, for example as described in our prior U.S. Pat. No. 6,299,447, the contents of which are incorporated herein by reference. The head 16 has an upper end 20 and an outer locating surface having first and second spaced annular retention rims or ribs 22,24, separated by an annular groove 25. It will be understood that the head may be provided with three or more spaced annular retention ribs in alternative embodiments. The ribs may be of the same diameter. However, in the illustrated embodiment, the uppermost rib 22 is of slightly smaller diameter than the lowermost ribs 24. The lowermost rib 24 has generally curved or rounded upper and lower faces which transition smoothly to the flat annular outer rim, as best illustrated in FIG. 3.

The female or retention member 14 is generally cup-shaped, having an upper end 26 and a skirt 28 projecting from the upper end. The skirt 28 has an outwardly curved or bulging outer face, and an inner face which is of a shape designed for releasable snap engagement over the spaced retention ribs 22,24 of the abutment member 12. The skirt has a rounded lower end 34, a first annular indented region or groove 35 on the inner face adjacent the lower end, an inwardly projecting annular rib 36, and a second generally indented region 38 above rib 36, region 38 being of slightly smaller diameter than region 35. The indented regions 35 and 38 are designed for snap engagement over the corresponding retention ribs or surfaces 24,22, respectively, on the head 16, while the rib 36 fits into the groove 25, as best illustrated in FIG. 3. The resilience of the female member allows it to stretch and snap over the stacked retention surfaces on the male or abutment member 12, after which it will be securely but releasably held in place. By making the upper rib 22 of slightly smaller diameter, the lowermost indented region 35 will be able to snap over it easily, making it easier for a patient to place the attachment.

The metal cap 15 has outer ribs 49 and is secured at an appropriate location in the partial denture or other denture appliance, as is known in the field. The cap 15 has an open end 42 leading into a curved internal cavity for receiving the female or retention member 14. The curvature on the inside surface 44 of the side wall of the cavity is designed to retain the member 14 and prevent it from coming out accidentally as the denture is removed from the mouth. At the same time, the cap has a swivelling engagement with the male member 14. Thus, the retentive nylon female member 14 remains in static contact with the abutment member 12, while the metal denture cap 15 has a full range of rotational movement over the member 14. This provides a resilient connection for the denture without any resultant loss of retention.

The male or abutment member 12 will be placed at the desired location in a patient's mouth in a conventional manner. The root will first be prepared to receive the stem 18. It should be noted that two or more such abutments may be required for a particular denture, depending on its size. Once all roots are prepared, the male abutment members 12 are all cemented in place, with the majority of the outer locating surface of each male member extending above the tissue or gum level, so that the corresponding female or retention members can snap into place without interference.

FIG. 4 illustrates a modified male or abutment member 45 for securing to an implant rather than an existing non-vital root. The abutment member can be used with the same female or retention member 14 and cap 15 as illustrated in FIGS. 1 to 3. Abutment member 45 has a head 46 having a similar outer locating surface to head 16 of the previous embodiment, and a threaded stem 48 for engagement in a corresponding threaded bore in the implant. The lower end face 50 of head 46 will be provided with a recess (not illustrated) for engagement over a matching projection, such as a hex projection, of the implant on which it is to be secured. It will be understood that the shape and dimensions of the recess will be dependent on the type of implant. As in the case of the root retained member 12, the head 46 of the implant retained member 45 has a generally flat upper end face 52, and a pair of spaced, projecting annular retention surfaces or ribs 53,54 separated by an annular indent 55, with the shape and dimensions of the surfaces 53,54 and indent 55 being similar or identical to those of the ribs 22,24 and indent 25 of FIGS. 1 to 3, so that the same retention member 14 can be snap engaged over head 45 in the same manner as indicated in FIGS. 1 and 3.

It will be understood that male or abutment members as illustrated in FIGS. 1 to 4 may be provided with an angle offset to accommodate divergent tooth roots or implant placements, as described in U.S. Pat. Nos. 6,030,219 and 6,299,447 referred to above, but with the same heads having double stacked retention surfaces to provide greater retention surface area without requiring an inside retention. In the case of both straight and angularly offset abutment members, the head can be made of smaller diameter than a prior art female member with both an inner retention socket and an outer retention formation. This permits the abutment members to be installed in anterior areas of the jaw, where a partial denture or overdenture extends over such areas.

Figure 6:
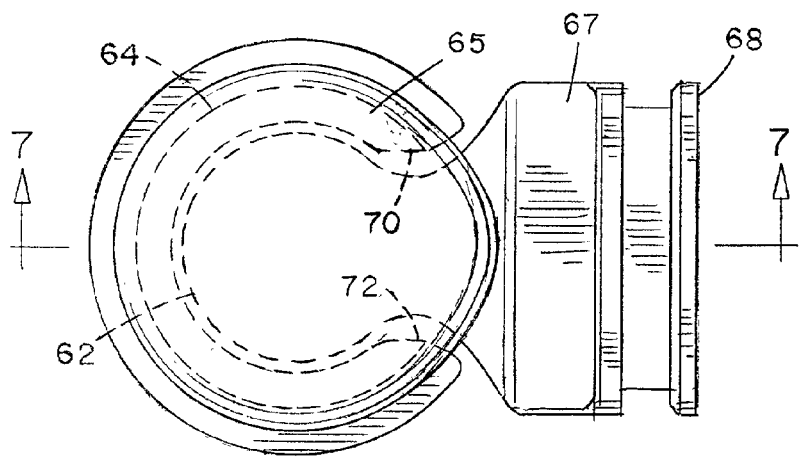
FIG. 6 is a top plan view of the assembled components of FIG. 5.
Figure 7:
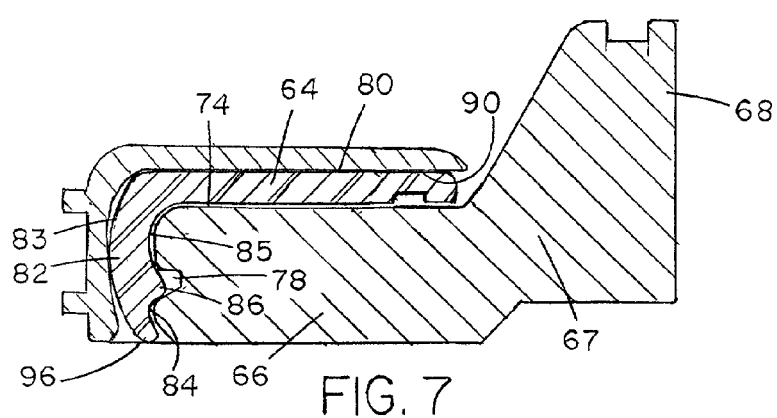
FIG. 7 is a cross-section on the lines 7—7 of FIG. 6.

FIGS. 5 to 7 illustrate a dental attachment assembly 60 for attachment to an adjacent tooth rather than to a root or implant. Assembly 60 basically comprises a male or abutment member 62, a female or retention member 64, and a swivelling cap 65. The abutment or anchor member 62 has a generally cylindrical head 66, and a distal extension or connecting arm 67 extending radially from the head 66 and terminating in a plate portion 68 which is secured in a suitable slot provided in an adjacent or abutment tooth. The female member 64 and cap 65 are of similar shape to those of the previous embodiment, but each has a downwardly opening slot or indent 70, 72, respectively, cut in one side which is of sufficient width for engagement over the distal extension or arm 67 of the anchor member 62 when the parts are secured together, as indicated in FIGS. 6 and 7.

As best illustrated in FIGS. 5 and 7, the head 66, as in the previous embodiments, has a flat upper end 74, and a pair of stacked, spaced annular projecting surfaces or ribs 75,76 separated by an annular indent 78. More than two stacked annular projecting surfaces may be provided in alternative embodiments for increased retention. The female or retention member 64 has a flat upper end surface 80 with a downwardly depending annular skirt 82 having a rounded outer surface 83 and an inner surface with a pair of spaced annular indents or grooves 84,85 for snap engagement over the respective ribs 75,76 in the head 66. Grooves 84,85 are separated by an annular ridge or rib 86 which engages in groove or indent 78 in the head when the parts are secured together, as indicated in FIG. 7.

The cap 65, as in the previous embodiment, has an inner recess or cavity for engagement over the outer surface 83 of the female or retention member 64, with a curved inner surface 88 for retaining the retention member 64 while permitting swivelling motion between the retention member and cap. The slot 72 terminates short of the upper end face 89 of the cap, leaving a flat inner face portion 90 at the upper end of slot 72, which acts as a stop against the opposing flat portion of the upper end face 80 of the retention member.

Figure 8:
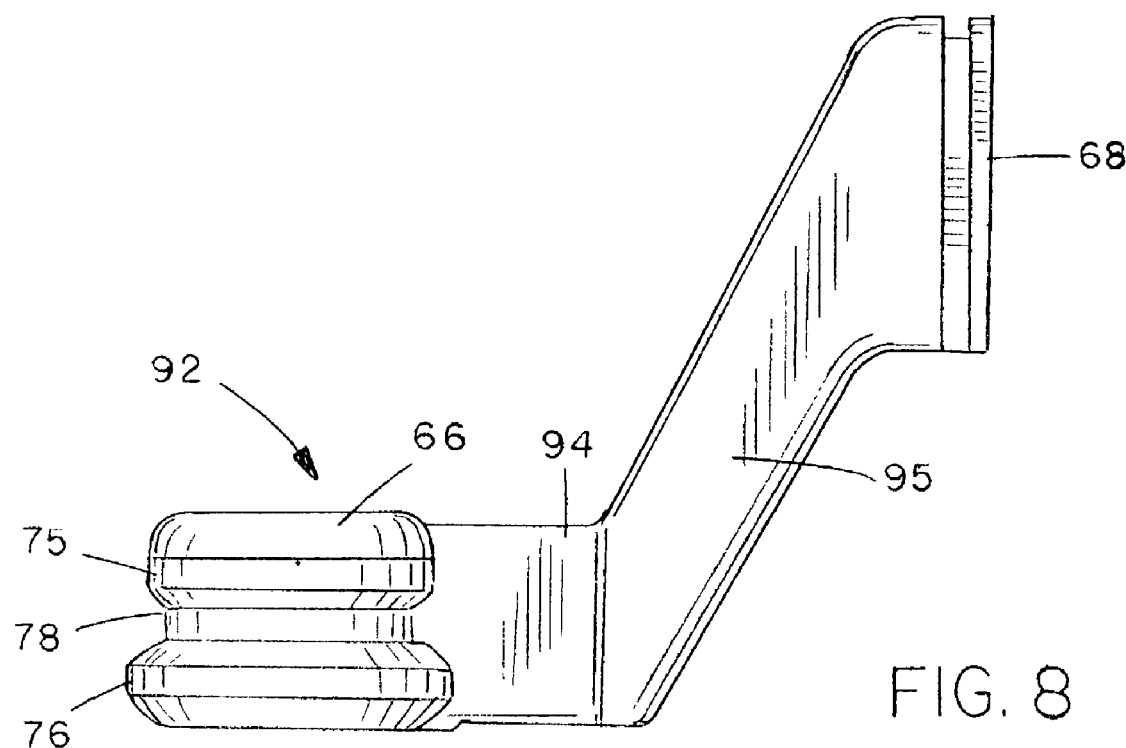
FIG. 8 is a side view of an extended anchor component.

FIG. 8 illustrates a modified male or abutment member 92 for use where there has been a greater amount of tissue or bone erosion. Member 92 will be used with the same female or retention member 64 and cap 65 as in FIGS. 5 to 7. Some parts of member 92 are identical to parts of member 62, and like reference numerals have been used as appropriate. However, the head 66 of member 92 is spaced a greater distance below the plate portion 68 to be attached to the abutment tooth, to allow for a lower installation position when required. Abutment members will typically be provided with at least three different drop down heights. Thus, the connecting flange or distal extension 94 connecting head 66 to plate portion 68 has a longer, steeper inclined connecting portion 95 than the distal extension 67 of FIGS. 5 to 7.

In the embodiment of FIGS. 5 to 7, after the male or abutment member 62 has been positioned appropriately and attached via plate portion 68 to an adjacent tooth, and the cap and male member have been secured in an indent at an appropriate location in a denture, the denture can be releasably engaged on the abutment member 62, and other abutment members placed elsewhere in the patient's mouth, as appropriate. The denture is pushed down so that the rounded lower end 96 of retention member 64 engages the top of the head 66, with the slots 70 and 72 aligned over the distal extension or connecting arm 67. This will tend to center the retention member over the head. The skirt of the retention member will then be urged outwardly so that the indent 84 snaps out over rib 75, and subsequently over the lower rib 76 as the inner indent 85 snaps over rib 75. Due to the reduced diameter of the upper rib 75, larger diameter indent 84 can snap easily over rib 75, and then over the matching rib 76. The upper end of the slot 70 will then be seated on top of the distal exension 67, while the upper end face 90 of the slot 72 will seat against the flat upper end face 80 of the retention member.

The horizontal stop between the cap 65 and the retention or female member 64 will prevent uplift of the partial denture or overdenture. The metal cap 65 can pivot over the male member 64, as described above in connection with the previous embodiment. However, the pivoting metal housing will contact and stop on the upper horizontal end face of the male member 64, thus preventing uplift of the denture flange.

With this arrangement, there will be no chance of the metal cap contacting the vertical plate or wall portion 68 of the abutment member 62 or adjacent surfaces of the abutment tooth. At the same time, the nylon female member will stay in secure, static contact with the cast abutment or male member 62, reducing wear of both the nylon female member and the abutment member, since there will be no constant rotation between these parts during mastication, and the only wear will be from removal and re-insertion of the denture. The pivoting action of the metal cap is directed in a controlled distal direction to avoid "fishtailing" of the partial denture, and to direct biting forces away from the abutment tooth, to be shared by the support of the mucosal tissue underneath the posterior flange of the partial denture.

Figure 9:
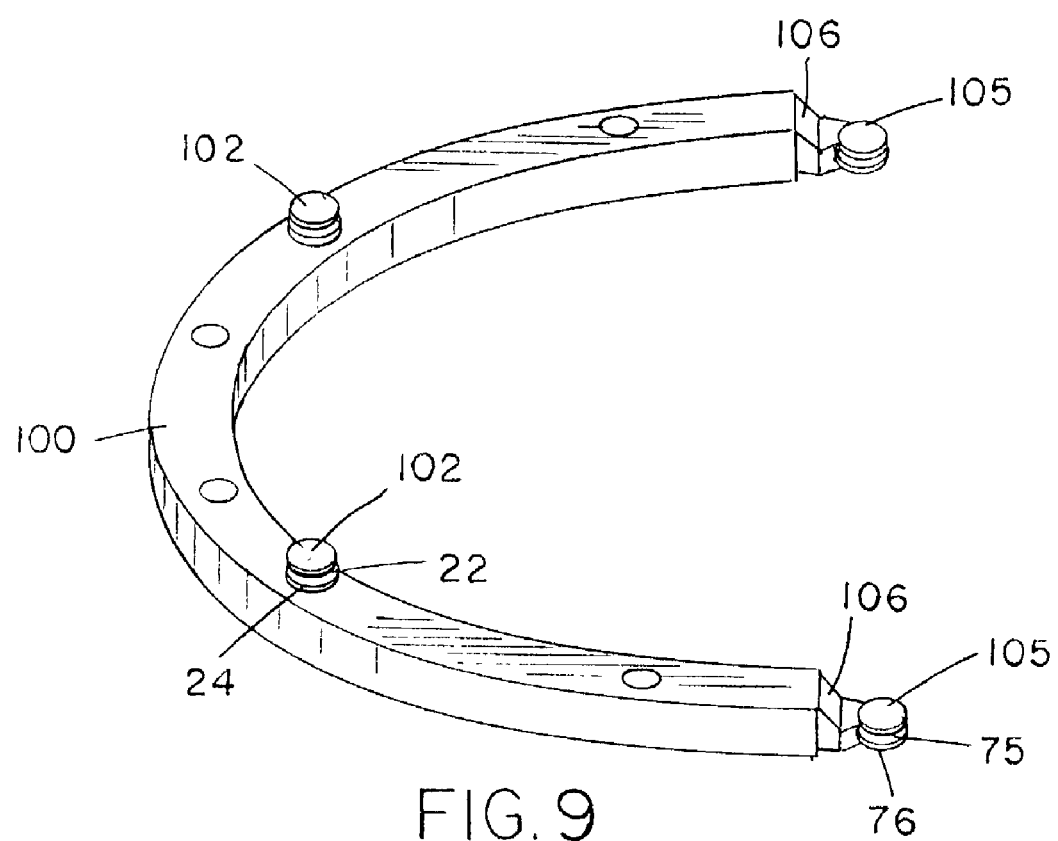
FIG. 9 is a perspective view of a multiple anchor cast bar.

FIG. 9 illustrates part of an implant retained, cast bar 100 forming part of a denture attachment assembly according to another embodiment of the invention. The bar 100 will be secured in implants in a patient's jaw in a known manner, and is curved to follow the shape of the patient's upper or lower jaw. Male or abutment members 102 are cast at spaced locations on the bar. Each abutment member 102 is identical in shape to the head 12 of the first embodiment, and like reference numerals have been used for like parts as appropriate. Additionally, abutment members of the type illustrated in FIGS. 5 to 7 are secured at each end of bar 100, each member having a head 105 identical to head 62 of the previous embodiment, and a radially and upwardly extending distal extension arm 106 securing the head 105 to the respective end of the bar.

The members 105 are otherwise identical to the members 62, and each head has vertically stacked retention surfaces or ribs 75 and 76 separated by groove 78. As before, three or more stacked retention surfaces may be provided in alternative embodiments. The distal extension arm 106 will be selected with an appropriate drop down dependent on the gum and jaw recession at the respective location in the jaw. An overdenture for attachment to the bar 100 will be provided with appropriately positioned caps 15 and retention or male members 14 for snap engagement over heads 102, and with caps 65 and female members 64 at opposite ends for snap engagement over heads 105, with appropriately positioned slots to engage over arms 106.

In each of the above embodiments, the provision of stacked retention surfaces between the abutment or male member and the retention or female member allows for external retention only with sufficient retention force, avoiding the need for internal retention between the members by means of a socket or indent on the male and a stem on the female for snap engagement in the socket. This allows the abutment and retention members, and thus the overall assembly, to be made with smaller diameters than was previously possible, making placement at smaller, anterior tooth locations possible. In one example of a root attachment assembly as illustrated in FIGS. 1 to 3, the overall diameter of the assembly (i.e. external diameter of the cap) was of the order of 0.10 to 0.20 inches, the diameter of the stem of the abutment member was of the order of 0.050 to 0.070 inches, and the height of the assembly above the tissue level was of the order of 0.080 to 0.090 inches. Similar dimensions will be possible for the implant attachment assembly, using the abutment member of FIG. 4, and for the castable bar embodiment of FIG. 9. In one example of a distal extension attachment assembly as illustrated in FIGS. 5 to 8, the overall diameter of the assembly (i.e. external diameter of the cap 65) was of the order of 0.10 to 0.20 inches, and the overall height of the assembly as illustrated in FIG. 7, i.e. from the lower face of member 66 to the upper face of cap 65, was of the order of 0.070 to 0.085 inches, suitably around 0.079 inches. The height of the end plate 68 is approximately the same as the height of the overall assembly of FIG. 7.

Thus, the overall diameter of the assembly, i.e. the abutment or male member, female member, and cap, is much less than for an assembly where there is both internal and external retention between the female and male member, for example as described in prior U.S. Pat. Nos. 6,030,219 and 6,299,447 referred to above. This means that the attachment assembly can be mounted at anterior locations in the mouth and the corresponding denture or dental appliance, where the teeth, roots, and artificial teeth to replace such a tooth, will be of smaller dimensions. The multiple stacked retention surfaces provide a greater retention wear surface area with a smaller diameter than a dual inside/outside retention as was used in previous attachment assemblies.

In addition to the reduced diameter, the multiple retention surfaces provide greater retention surface area and corresponding reduction in the loss of retention surface. Thus, the lifetime of the assembly before effective retention force is lost may be increased. Although two stacked retention surfaces, and a corresponding number of annular indents on the female member, are illustrated, it will be understood that a greater number of stacked retention surfaces and mating indents may be provided in alternative embodiments. Although the retention ribs may be of the same diameter, the uppermost or outermost rib in the exemplary embodiments above is of slightly smaller diameter than the outer rib or ribs. This allows for a denture to be attached more easily by the patient, since the first, larger diameter indent on the female will snap readily over the first rib. Subsequently, both indents snap over the matching ribs. The lowermost rib can thus have more retentive hold, and the denture will be easier to place than to remove. This reduces the risk of accidental dislodgement. The retention force can be regulated during manufacture simply by varying the rib and corresponding indent diameters.

The lower rib has a curved upper and lower surface providing a smooth transition with the outer "flat" annular rim of the rib. This avoids sharp edges which could abrade the plastic nylon female surfaces as the female is snapped on and off.

Although some exemplary embodiments of the invention have been described above by way of example only, it will be understood by those skilled in the field that modifications may be made to the disclosed embodiments without departing from the scope of the invention, which is defined by the appended claims.

We claim:

1. A dental attachment assembly, comprising:
   an abutment member for attachment to a tooth root, implant, or adjacent tooth, the abutment member having a central axis, a first end, and an outer locating surface projecting away from the first end, the outer locating surface having at least two axially spaced retention portions;
   a retention member having a first end and a skirt extending from the first end having an inner surface for engagement over the outer locating surface of the abutment member, the inner surface of the skirt having at least two axially spaced, snap engaging formations for releasable snap engagement with the respective retention portions of the abutment member; and
   the axially spaced retention portions on the outer locating surface of the abutment member comprising two generally rounded, annular projections and the axially spaced, snap engaging formations on the inner surface of the skirt comprising two spaced, annular grooves for snap engagement over the annular projections on the abutment member.

2. The assembly as claimed in claim 1, wherein the abutment member has a head on which the spaced retention portions are located, and a stem extending axially away from the head for engagement in a socket in a tooth root or implant.

3. The assembly as claimed in claim 1, wherein the abutment member has a radial extension for securing to an adjacent tooth.

4. The assembly as claimed in claim 1, wherein the abutment member is of solid construction and has no through bores.

5. The assembly as claimed in claim 1, including a cap for securing in a recess in a dental appliance, the cap having a cavity for releasable snap engagement over the retention member, the cap and retention member having respective rounded inner and outer surfaces for permitting swiveling of the cap over the abutment member.

6. The assembly as claimed in claim 1, wherein the skirt has a lower edge for facing the abutment member as the retention member is engaged over the abutment member, the lower edge being of rounded shape.

7. The assembly as claimed in claim 1, wherein the abutment member has a radial extension from one side of its outer locating surface, and a plate at the outer end of the extension for securing in a cavity in an adjacent tooth surface.

8. The assembly as claimed in claim 7, including a cap for securing in a recess in a dental appliance, the cap having a cavity for releasable snap engagement over the retention member, the cap and retention member having respective rounded inner and outer surfaces for permitting swiveling of the cap over the abutment member.

9. The assembly as claimed in claim 8, wherein the retention member has a first slot and the cap has a second slot for engaging over the radial extension to allow the retention member skirt to engage over the outer locating surface of the abutment member.

10. The assembly as claimed in claim 1, including a bar having a curvature for following the curvature of at least part of a patient's mouth, the bar having opposite faces, the bar having a plurality of spaced securing devices projecting in a first direction from one face of the bar for securing the bar to a plurality of roots or implants, a plurality of said abutment members secured at spaced intervals to an opposite face of the bar and projecting in a second direction opposite to the first direction, and a plurality of said retention members for releasable snap engagement with said respective abutment members.

11. The assembly as claimed in claim 10, wherein the bar is of predetermined shape and dimensions to extend around the patient's jaw and has opposite ends, a distal extension projecting from each end of the bar, and an additional abutment member is secured to each distal extension, the assembly further comprising two additional retention members for releasable snap engagement with the respective additional abutment members, each additional retention member having a slot for engagement over the distal extension as the additional retention member is snapped over the additional abutment member.

12. The assembly as claimed in claim 1, wherein the retention portions are of the same diameter.

13. The assembly as claimed in claim 1, wherein the retention portions comprise an uppermost retention portion adjacent the first end of the abutment member and at least one lower retention portion, the uppermost retention portion having a diameter less than the lower retention portion, and the snap engaging formations having diameters substantially matching the diameters of the respective retention portions.

14. The assembly as claimed in claim 1, wherein at least one of the retention portions has a substantially flat outer rim, an upper curved portion, and a lower curved portion, the curved portions leading smoothly into the outer rim with no sharp edges.

15. A dental attachment assembly, comprising:
an abutment member for attachment to a tooth root, implant, or adjacent tooth, the abutment member having a central axis, a first end, and an outer locating surface projecting away from the first end, the outer locating surface having at least two axially spaced retention portions;

the abutment member having a radial extension from one side of its outer locating surface, and a plate at the outer end of the extension for securing in a cavity in an adjacent tooth surface;

a retention member having a first end and a skirt extending from the first end having an inner surface for engagement over the outer locating surface of the abutment member, the inner surface of the skirt having at least two axially spaced, snap engaging formations for releasable snap engagement with the respective retention portions of the abutment member;

a cap for securing in a recess in a dental appliance, the cap having a cavity for releasable snap engagement over the retention member, the cap and retention member having respective rounded inner and outer surfaces for permitting swiveling of the cap over the abutment member;

the retention member having a first slot and the cap having a second slot for engaging over the radial extension to allow the retention member skirt to engage over the outer locating surface of the abutment member; and the retention member having an upper flat, generally horizontal surface portion above the first slot, and the second slot having an upper end, the cap having a downwardly facing, generally horizontal surface portion at the upper end of said second slot, the downwardly facing, generally horizontal surface portion of the cap and the upper flat, generally horizontal surface portion of the retention member together forming a horizontal stop to prevent uplift of a partial denture in which the cap is secured.

16. The assembly as claimed in claim 15, wherein the horizontal stop prevents the cap from contacting the plate or the abutment tooth in which the plate is secured.

* * * * *